US010315968B2

United States Patent
Janda et al.

(10) Patent No.: US 10,315,968 B2
(45) Date of Patent: Jun. 11, 2019

(54) PROCESS FOR STEAM CRACKING HYDROCARBONS

(71) Applicant: ExxonMobil Chemical Patents Inc., Baytown, TX (US)

(72) Inventors: Gary F. Janda, Houston, TX (US); David B. Spicer, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/817,812

(22) Filed: Nov. 20, 2017

(65) Prior Publication Data

US 2018/0170832 A1    Jun. 21, 2018

Related U.S. Application Data

(60) Provisional application No. 62/436,626, filed on Dec. 20, 2016.

(51) Int. Cl.
| | | |
|---|---|---|
| *C07C 4/04* | (2006.01) | |
| *C07C 4/02* | (2006.01) | |
| *C07C 4/06* | (2006.01) | |
| *C07C 5/327* | (2006.01) | |
| *C10G 11/00* | (2006.01) | |

(52) U.S. Cl.
CPC ............. *C07C 4/04* (2013.01); *C07C 5/327* (2013.01); *C10G 11/00* (2013.01)

(58) Field of Classification Search
CPC ................ C07C 4/04; C07C 4/02; C07C 4/06
See application file for complete search history.

(56) References Cited

U.S. PATENT DOCUMENTS 4,426,278 A  *  1/1984  Kosters ............... C10G 9/14
                                              208/130
2016/0168478 A1     6/2016  Spicer et al.

OTHER PUBLICATIONS

Rosli, M.N. et al, "Simulation of ethane steam cracking with severity evaluation", Materials Science and Engineering, vol. 162, No. 1, pp. 1-6, Nov. 1, 2016.
Moreira, J.V., "Steam Cracking: Kinetics and Feed Characterisation", Instituto Superior Tecnico, Lisbon, Portugal (URL:https://fenix.tecnico.ulisboa.pt/downloadFile/1126295043834327/JVM_ExtendedAbstract.pdf . pp. 1-10, Nov. 1, 2015.
Yancheshmeh, M.S.S. et al. "Modeling of ethane pyrolysis process: A study on effects of steam and carbon dioxide on ethylene and hydrogen productions", Chemical Engineering Journal. vol. 215-216, pp. 550-560, Nov. 12, 2012.

* cited by examiner

*Primary Examiner* — Youngsul Jeong (57) ABSTRACT

A steam cracking process for converting hydrocarbons into smaller hydrocarbons, particularly olefins, in a tube reactor comprising a convection section, a cross-over section, and a radiant section. The process includes heating the fluid mixture inside the tube to a temperature at the end of the convection section where significant cracking occurs in the cross-over section. The high convection section and cross-over section temperatures allow for lower tube wall temperature in the radiant section resulting in less coke deposition on the inner wall of the tube, and hence extended run-lengths between adjacent decoking sessions.

25 Claims, 1 Drawing Sheet

PROCESS FOR STEAM CRACKING HYDROCARBONS

PRIORITY CLAIM

This application claims the benefit of Provisional Application No. 62/436,626, filed Dec. 20, 2016, the disclosures of which is incorporated herein by reference.

FIELD OF THE INVENTION

The present invention relates to processes for steam cracking hydrocarbons. In particular, the present invention relates to processes for producing alkenes from steam cracking hydrocarbons in a steam cracking furnace.

BACKGROUND OF THE INVENTION

Steam cracking is the major commercial process for the production of light olefins, especially ethene and propene. In typical steam cracking, the hydrocarbon feed is first preheated and mixed with dilution steam in the convection section of the furnace. After preheating in the convection section, the vapor feed/dilution steam mixture is rapidly heated in the radiant section to achieve the desired thermal cracking. After the desired degree of thermal cracking has been achieved in the radiant section, the furnace effluent is rapidly quenched in either an indirect heat exchanger or by the direct injection of a quench oil stream.

An undesirable byproduct of the cracking process is often the deposition of carbon deposits, commonly referred to as "coke," on the inner surfaces of the radiant tubes of the furnace. Depending on the feedstock being cracked, coke may also be deposited in certain tubes in the convection section, or in the quench system of the furnace.

Steam cracking furnace performance is most frequently limited by the build of coke inside the radiant tubes. The coke acts as a thermal insulator resulting in increasing radiant tube metal temperatures (TMT's) as a run progresses. Once the TMT's approach or reach the design limit, the furnace needs to be decoked.

The coke inside the tubes also causes a hydraulic restriction and higher coil pressure drop. When the pressure drop becomes high enough, the resulting higher backpressure causes a loss-of-critical-flow at the critical flow nozzles located at the inlet of the radiant section. Once critical flow is lost for a particular tube, the flow rate through that tube will be reduced which results in a higher coking rate, which aggravates the hydraulic restriction further. This cycle continues rapidly and a decoke operation will be required.

It is desirable to reduce the radiant tube metal temperatures without a significant adverse impact on throughput and production.

One method for reducing the radiant TMT's is to raise the process duty of the furnace convection section so that the required radiant duty is lower for a given feed rate, S/HC, and conversion. Raising the duty of the convection section will of course raise the temperature of the process gas leaving the convection section. The temperature of the process gas leaving the convection section is referred to as the cross-over temperature ("XOT", not to be confused with the term used in industry to denote radiant coil outlet temperature "COT").

The perception in industry seems to be that the temperatures in the convection section need to be limited such that any significant thermal cracking does not occur therein. The concerns are likely based on the assumed drawbacks that thermal cracking in the convection section or cross-over is too unselective for ethene, and that it will cause coking inside the convection section tubes.

SUMMARY OF THE INVENTION

It was discovered that, surprisingly, raising the XOT such that a reasonable amount of thermal cracking happens in the convection section and cross-over piping has the benefit of reducing radiant section TMT's with minimal drawbacks of reduced ethene selectivity and coking propensity inside the convection section tubes. The impact on overall furnace ethene selectivity is small to manageable, and is often offset economically by the production of valuable co-products. In addition, it was discovered that, surprisingly, there is usually little or no measurable coking in the convection section when XOT's and associated convection section cracking are high. Thus, one can use a high XOT to increase the time interval (run-length) between decoking operations for a set of fixed conditions (e.g., feed rate, stream to hydrocarbon ratio, conversion) due to lower TMT's. Alternatively, the feed rate and/or conversion can be raised while maintaining a similar TMT and/or furnace run-length.

Accordingly, the present invention provides a process for steam cracking hydrocarbon in a steam cracking furnace including a tube comprising a convection section, a cross-over section downstream of the convection section, and a heated radiant section downstream of the cross-over section, comprising: (i) feeding the hydrocarbon material and steam into the convection section to obtain a feed mixture; (ii) heating the hydrocarbon material mixture in the convection section to obtain a first fluid stream at a temperature T1 at the end of the convection section; (iii) passing the first fluid stream through the cross-over section to obtain a second fluid stream at the end of the cross-over section at a temperature T2; (iv) passing the second fluid stream through the radiant section to obtain a cracked fluid mixture at the end of the radiant section at a temperature T3, wherein: T3 is higher than T2 and T1; and T1 and T2 are selected such that significant cracking reaction occurs at least in a portion of the convection section and at least a portion of the cross-over section.

DETAILED DESCRIPTION OF THE INVENTION

Figure 1:
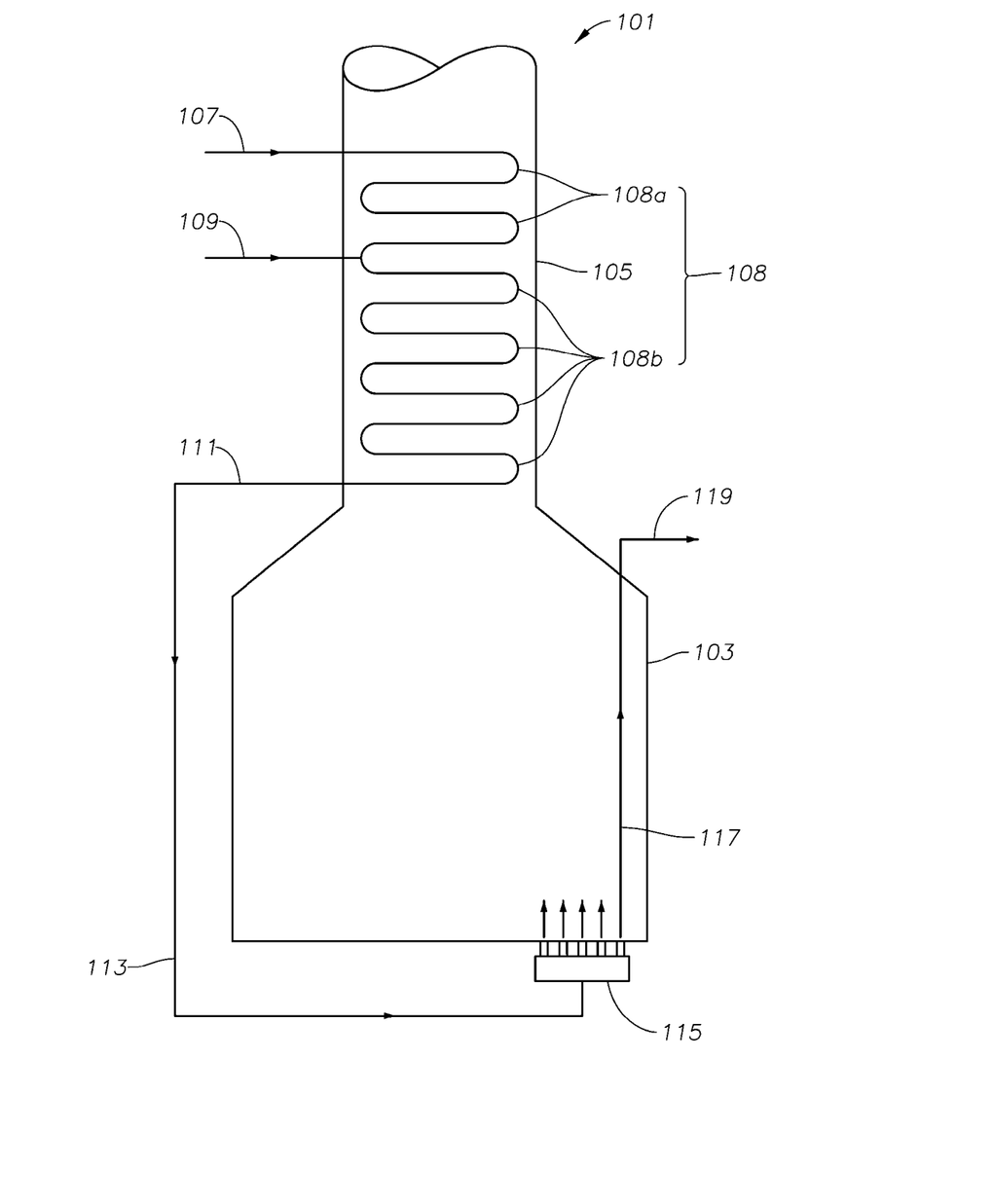
The FIGURE is a schematic illustration of a steam cracking furnace in operation to convert hydrocarbons to produce lighter hydrocarbons such as ethene and propene.

As used herein, the term "severity index" is defined as weight ratio of $C_3H_6$ to $CH_4$ in a cracked mixture. As used herein, a "Cm hydrocarbon" means a hydrocarbon having n carbon atoms in its molecular structure, where n is an integer; and "Cm to Cn hydrocarbons" means hydrocarbons having from m to n carbon atoms in the molecular structures thereof, where m and n are integers and m<n, and mixtures thereof.

The FIGURE schematically illustrates a typical steam cracking furnace 101 in operation. The furnace 101 includes a radiant fire box 103 in the lower portion thereof and a convection zone 105 in the upper portion thereof. A hydrocarbon feed stream 107 (comprising ethane, propane, butane, gas oil, or naphtha, and the like) is fed into the hydrocarbon inlet of an upstream portion 108a of convection section 108 of a steam cracking tube. A diluent steam stream 109 is fed into a downstream portion 108b of the convention section 108 at a location downstream of the hydrocarbon inlet to mix with the hydrocarbon feed stream. The combined hydrocarbon/steam stream travels downward along the convection section 108. Because of hot gas traveling upwards inside the firebox, the hydrocarbon/steam feed mixture inside the convection section is gradually heated up as it travels along the tube. When it reaches the end (location 111) of the convection section which is located immediately outside of the wall of furnace 101 as the first fluid stream, its temperature reaches T1° C. The end of the convection section is connected to the start of the cross-over section 113 of the steam cracking tube. The cross-over section is typically located outside of the wall of the furnace 101 to avoid heating the hydrocarbon and stream mixture to an exceedingly high temperature where substantial cracking can occur prematurely. At the end of the cross-over section, a second fluid stream at T2° C. is obtained. The cross-over section is thermally insulated to prevent excessive heat loss with or without active heating. Where no active heating is applied, T2 is typically slightly lower than T1 as a result of heat loss and/or endothermal cracking reactions occurring if T1 is sufficiently high. The cross-over section ends with one or more critical flow nozzles (at the location of 115), which are connected to a lower end of one or more vertical radiant tubes 117 (radiant section of the steam cracking tube) installed inside the walls of the radiant zone of the furnace 101. The steam cracking tubes 117 in the radiant section are typically heated externally by a series of flames generated by burners (not shown) installed on the floor of the fire box and/or the side walls of the fire box. Operating conditions can be chosen such that a majority of the heat supplied to the radiant tubes are by radiation instead of convection or conduction. The fluid stream inside the radiant tubes travel at a very high space velocity while being heated by the radiant heat from the flames. After a very short residence time in the vertical radiant tubes, at the end of the radiant tubes 119 which are located immediately outside of the furnace box 103, the fluid stream can reach a temperature of T3° C. significantly higher than T2 and T1, where the cracking of large hydrocarbon molecules to form small hydrocarbon molecules such as ethene, propene, and the like, are favored. The cracked fluid mixture stream 119 exiting the radiant section at location 109 can be quenched and subsequently separated to obtain the desired product fractions, such as ethene, propene, butadiene, and the like. Typically, in a steam cracking process, saturated hydrocarbon materials such as alkanes are fed into the process, and a cracked fluid mixture comprising higher concentrations of alkenes, typically having fewer carbon atoms and/or smaller molecular weight in molecules thereof than those in the hydrocarbon materials than the hydrocarbon feed, is obtained.

In the past, the temperature of the hydrocarbon/steam feed mixture stream inside the convection section has been typically controlled at a low level such that significant cracking of hydrocarbon molecules does not occur. Thus, the concentration of olefins in the first fluid stream at the end of the convection section typically is not much higher than in the hydrocarbon/steam feed mixture at the location where the hydrocarbon feed and the steam stream is first admixed. Alternatively, the concentration of the saturated hydrocarbon material in the first fluid stream at the end of the convection section is typically not much lower than in the hydrocarbon/steam feed mixture at the location where the hydrocarbon feed and the steam stream is first admixed. As discussed above, such lower temperature operation in the convection section was chosen due to the assumed drawbacks of a higher-temperature operation in the convection section: (i) a higher coking propensity in the convection section and the cross-over section if substantial steam cracking is allowed to occur therein; and (ii) a subsequently lower temperature in the radiant section if a higher convection section temperature is used, which would be unfavorable to the conversion from ethane to ethene.

However, as indicated by the many examples given below, the present inventors have found, in a surprising manner, that even if the temperature in the convection section, especially the downstream portion thereof close to the cross-over section, is sufficiently high to allow significant cracking to occur therein, coking in the convection section and cross-over section does not increase to an unacceptable level. In addition, the yield of ethene did not decrease to an unacceptable level in the overall process. Furthermore, surprisingly, at least in the case of ethane steam cracking, the yield of valuable fractions of other hydrocarbons such as C5 and C6 olefins can increase, which can compensate the slightly decreased yield of ethene. Moreover, a higher temperature T1 at the end of the convection section means a higher temperature T2 in the cross-over section, and a higher temperature of the second fluid stream entering into the radiant section of the tube, thus enabling a lower tube metal temperature (TMT) of the tube in the radiant section during normal operation, thereby extending the time interval (run-length) between adjacent decoking operations required.

The Hydrocarbon Material

The process of the present invention can be effectively and efficiently used for the conversion of various types of hydrocarbon feed materials rich in aliphatic hydrocarbons into lighter hydrocarbons rich in olefins. To that extent, the hydrocarbon material fed into the furnace can contain ethane as a major component. For example, the fresh hydrocarbon material can contain, by weight of the total fresh feed, from a1% to a2%, of ethane, where a1 and a2 can be, independently, 50, 55, 60, 65, 70, 75, 80, 85, 90, 91, 92, 93, 94, 95, 96, 97, 98, 99, 100, as long as a1<a2.

In an alternative process of the present invention, the hydrocarbon material fed into the furnace can contain butane as a major component. For example, the fresh hydrocarbon material an contain, by weight of the total fresh feed, from b1% to b2%, of butane, where b1 and b2 can be, independently, 50, 55, 60, 65, 70, 75, 80, 85, 90, 91, 92, 93, 94, 95, 96, 97, 98, 99, 100, as long as b1<b2.

In another alternative process of the present invention, the hydrocarbon material fed into the furnace can contain naphtha as a major component. As used herein, "naphtha" means a mixture of C5-C10 aliphatic hydrocarbons. For example, the fresh hydrocarbon material can contain, by weight of the total fresh feed, from c1% to c2%, of naphtha, where c1 and c2 can be, independently, 50, 55, 60, 65, 70, 75, 80, 85, 90, 91, 92, 93, 94, 95, 96, 97, 98, 99, 100, as long as c1<c2.

In another alternative process of the present invention, the hydrocarbon material fed into the furnace can contain gas oil as a major component. As used herein, "gas oil" means a mixture of C10-C20 hydrocarbons. A typical gas oil contains at least 50 wt % of C10-C20 alkanes. For example, the fresh hydrocarbon material can contain, by weight of the total fresh feed, from d1% to d2%, of gas oil, where d1 and d2 can be, independently, 50, 55, 60, 65, 70, 75, 80, 85, 90, 91, 92, 93, 94, 95, 96, 97, 98, 99, 100, as long as d1<d2.

In practical manufacture operation, the reaction conditions are controlled such that a majority, but not 100% of conversion per pass of the feed hydrocarbon is achieved. Thus, the cracked fluid mixture at the exit of the radiant section typically contains a non-negligible amount of the hydrocarbon material fed into the cracking furnace. Upon separation from the useful product, the unreacted hydrocarbon may be recycled to the steam cracking furnace in order to increase the overall conversion of the process.

The Steam Cracking Conditions

Typically, the heavier the hydrocarbon material fed into the steam cracking furnace, the lower the operation temperature, and the heavier the cracked fluid mixture tends to be. As indicated above, the process of the present invention can be used for steam cracking of various hydrocarbon materials as the fresh feed, to obtain different cracked products, particularly olefins with different molecular sizes.

In general, in the process of the present invention, temperature at the lower portion of the convection zone, particularly at the end thereof (T1), is controlled at a sufficiently high temperature, such that significant cracking reactions occur in the lower portion of the convection section and the cross-over section before the second fluid stream enters into the radiant section, where a great majority of the steam cracking takes place. Thus, compared to the feed mixture including all fresh feed, recycled hydrocarbon, and steam assuming no chemical reactions having taken place, the first fluid mixture exiting the end of the convection section and entering the cross-over section tends to have an overall olefins concentration. Thus, assuming the feed comprises olefins at a total concentration of C0 mol % based on the total moles of the fluid species in the feed before any cracking reaction occurs; the first fluid stream comprises olefins at a total concentration of C1 mol % based on the total moles of the fluid species therein; then $g1\% \leq C1-C0 \leq g2\%$, where g1 and g2 can be, independently, 3, 4, 5, 6, 7, 8, 9, 10, 11, 12, 13, 14, 15, 16, 17, 18, 19, 20, as long as g1<g2.

As indicated above, typically T2<T1<T3. Where the cross-over section is not actively heated and merely thermally insulated outside of the furnace box, due to the endothermal nature of the cracking reactions, the temperature of the fluid stream inside the cross-over section decreases from the beginning to the end. Thus, the temperature differential T1−T2 can be in the range from e1 to e2° F., where e1 and e2 can be, independently, 75, 70, 65, 60, 55, 50, 45, 40, 35, 30, 25, 20, 15, 10, or even 5, as long as e1<e2. In the cross-over section of the reactor, additional cracking is allowed to continue because of the relatively high temperature T1 of the first fluid mixture entering the cross-over section, even if T2<T1. Thus, assuming the feed comprises olefins at a total concentration of C0 mol % based on the total moles of the fluid species in the feed before any cracking reaction occurs; the second fluid stream comprises olefins at a total concentration of C2 mol % based on the total moles of the fluid species therein; then $h1\% \leq C2-C0 \leq h2\%$, where h1 and h2 can be, independently, 5, 6, 7, 8, 9, 10, 11, 12, 13, 14, 15, 16, 17, 18, 19, 20, 21, 22, 23, 24, 25, as long as h1<h2.

The temperature differential T3−T2 can be in the range from f1 to f2° F., where f1 and f2 can be, independently, 100, 150, 200, 250, 300, 350, 400, 450, or 500, as long as f1<f2. This significantly higher T3 would lead to a majority of the cracking reactions in the radiant sections even though the residence time therein is typically very short, e.g., on the order of milliseconds to hundreds of milliseconds.

The cracking conditions, especially those in the radiant section, are chosen to favor the thermal pyrolysis of the aliphatic hydrocarbon molecules in the feed material to produce smaller, unsaturated hydrocarbon molecules and hydrogen in the cracked fluid mixture. The unsaturated hydrocarbons tend to have higher economic value than the aliphatic feed and used as industrial raw materials for making additional materials such as polymers.

At the end of the radiant section, the cracked fluid mixture is typically quenched immediately by a heat exchanger or by the injection of a quenching fluid stream. The quenched fluid stream is at a temperature where significant chemical reactions between and among the chemical species in the cracked fluid mixture is substantially stopped, preventing the formation of undesirable compounds that may form coke. The cracked fluid mixture can be separated in a downstream vessel by conventional methods such as condensation and evaporation to obtain various fractions: hydrogen, desirable unsaturated hydrocarbon fractions, and residual aliphatic hydrocarbons. The residual aliphatic hydrocarbons may be recycled into the steam cracking reactor, where it is further converted into desirable products, or alternatively, it may be combusted as a fuel for, e.g., producing the flames that heat the steam cracking furnace, particularly the radiant section.

A particularly undesirable byproduct in the steam cracking reactor is coke, a complex mixture of hydrocarbons having much higher boiling temperatures than the hydrocarbon feed material, which tend to deposit on the inner surface of the reactor tubes. Buildup of a coke layer over time can reduce heat transfer from the tube wall to the fluid stream inside, increase pressure differential from the inlet to the outlet of the tube coil, and lead to reactor wall corrosion by carbonization of the tube metal. To compensate the reduction of heat transfer resulting from coke deposition, higher tube external wall temperature is necessary, which can further aggravate coke formation. A steam cracking furnace is designed to operate only under a maximal pressure drop and a maximal tube wall temperature. When either limit is reached, the reactor has to cease operation and a decoking operation is required. It is highly desirable to reduce coke formation and deposition in order to extend the run-lengths of normal operations and minimize decoking events to the extent possible.

Reducing radiant section external wall temperature during normal operation of the reactor favors the reduction of coke formation. However, it is also generally detrimental to the conversion of the aliphatic hydrocarbons in the radiant section because of the highly endothermal nature of the reactions, and the selectivity toward desired products especially olefins in the radiant section.

One method to compensate for the reduced conversion and selectivity in the radiant section is to increase the temperature of the fluid stream in at least a portion of the convection section and the cross-over section such that a significant level of thermal cracking reactions occur before the radiant section. Historically, it was perceived that doing so would lead to undesirable level of coke deposition in the convection section and the cross-over section, given the residence time in these sections and conditions (particularly, a medium temperature between the high temperature in the radiant section and the low temperature of the cracked fluid mixture after quenching). However, surprisingly, the present inventors found that, by increasing the convection section temperature and reducing the radiant section temperature, the disadvantages of coke deposition before the radiant section and the overall reduction of conversion and selectivity of the reactor are acceptable, while the advantage of reduced coking deposition in the radiant section is substantial.

By using the process of the present invention, the decoking interval (defined as the run-length of the operation of a furnace between two adjacent decoking sessions) of the furnace can be extended by at least 10% (or at least 50%, 80%, 100%, 150%, 200%, 300%, 400%, or even 500%), compared to a process where the convection section and the cross-over section are operated at a temperature at which essentially no cracking occurs of the major component in the hydrocarbon material fed into the reactor, all other process parameters being held equal.

Ethane Steam Cracking

For ethane cracking, preferred fresh feed to the steam cracking reactor comprises from 50-100 mol % (e.g., 50, 55, 60, 65, 70, 75, 80, 85, 90, 95, 96, 97, 98, 99, 100 mol %) of ethane. As a minor component, propane may be present in the total hydrocarbon feed material as well, e.g., at a concentration from 5% to 50% by mole (e.g., 5, 10, 15, 20, 25, 30, 35, 40, 45, 50 mol %) of the total hydrocarbon feed. Under the cracking conditions, especially in the radiant section where the temperature is high, the cracking of ethane and propane are favored to produce methane, ethene, propene, hydrogen, acetylene, methylacetylene, which are smaller in molecular weight than ethane and/or propane. Larger molecules, such as C4, C5, and C6 hydrocarbons, may be produced as well, but typically at low concentrations. Upon separation in down-stream processes, C4, C5, and C6 olefins and aromatics can be obtained as valuable byproducts, and residual ethane and propane can be recycled to the steam cracking furnace as a portion of the overall feed.

T1 can be in the range from T1(ethane)1 to T1(ethane)2° F., where T1(ethane)1 and T1(ethane)2 can be, independently, 1300, 1325, 1350, 1375, 1400, 1405, 1410, 1415, 1420, 1425, 1430, 1435, as long as T1(ethane)1<T1(ethane)2;

T2 can be in the range from T2(ethane)1 to T2(ethane)2° F., where T2(ethane)1 and T2(ethane)2 can be, independently, 1275, 1300, 1325, 1350, 1375, 1400, 1410, 1420, 1430, as long as T2(ethane)1<T2(ethane)2; and T3 can be in the range from T3(ethane)1 to T3(ethane)2° F., where T3(ethane)1 and T3(ethane)2 can be, independently, 1500, 1525, 1550, 1575, 1600, 1625, 1650, 1675, 1700, 1725, 1750, 1775, 1800, as long as T3(ethane)1<T3(ethane)2.

The conversion of ethane in the process of the present invention can be desirably high, generally higher than 50% and lower than 80%. At higher than 80%, the selectivity toward ethene can be low. Thus, the conversion of ethane can be from Con(1)% to Con(2)%, where Con(1) and Con(2) can be, independently, 60, 62, 64, 66, 68, 70, 72, 74, 76, 78, 80, as long as Con(1)<Con(2).

In the steam cracking process of the present invention for ethane, it is highly desirable that the total concentration of C5 and C6 olefins, dienes and benzene in the cracked fluid mixture is in a range from x1 mol % to x2 mol % based on the total moles of different species therein, where x1 and x2 can be, independently, 1.0, 1.5, 2.0, 2.5, 3.0, 3.5, 4.0, 4.5, 5.0, 5.5, 6.0, 6.5, 7.0, 7.5, and 8.0, as long as x1<x2.

In the steam cracking process of the present invention for ethane, it is highly desirable that process has a total severity index (SI) in the cracked fluid mixture in a range from s1 to s2, where s1 and s2 can be, independently, 0.50, 0.55, 0.60, 0.65, 0.70, 0.75, 0.80, 0.85, 0.90, 0.95, 1.00, 1.05, 1.10, 1.15, 1.20, 1.25, as long as s1<s2.

Propane Steam Cracking

For propane cracking, preferred fresh feed to the steam cracking reactor comprises from 50-100 mol % (e.g., 50, 55, 60, 65, 70, 75, 80, 85, 90, 95, 96, 97, 98, 99, or 100 mol %) of propane. As a minor component, ethane may be present in the total hydrocarbon feed material as well, e.g., at a concentration from 5% to 50% by mole (e.g., 5, 10, 15, 20, 25, 30, 35, 40, 45, 50 mol %) of the total hydrocarbon feed. As another minor component, butane may be present in the total hydrocarbon feed material as well, e.g., at a concentration from 0% to 10% by mol of the total hydrocarbon feed. Under the cracking conditions, especially in the radiant section where the temperature is high, the cracking of propane, butane and ethane are favored to produce methane, ethene, propene, hydrogen, acetylene, and methylacetylene, which are smaller in molecular weight than propane. Larger molecules, such as C4, C5, and C6 hydrocarbons, may be produced as well, but typically at low concentrations. Upon separation in down-stream processes, C4, C5, and C6 olefins and aromatics can be obtained as valuable byproducts, and residual propane, ethane and butane can be recycled to the steam cracking furnace as a portion of the overall feed.

T1 can be in the range from T1(propane)1 to T1(propane)2° F., where T1(propane)1 and T1(propane)2 can be, independently, 1200, 1225, 1250, 1275, 1300, 1325, 1350, 1375, 1400, 1405, 1410, and 1415, as long as T1(propane)1<T1(propane)2;

T2 can be in the range from T2(propane)1 to T2(propane)2° F., where T2(propane)1 and T2(propane)2 can be, independently, 1175, 1200, 1225, 1250, 1275, 1300, 1325, 1350, 1375, 1400, and 1410, as long as T2(propane)1<T2(propane)2; and T3 can be in the range from T3(propane)1 to T3(propane)2° F., where T3(propane)1 and T3(propane)2 can be, independently, 1525, 1550, 1575, 1600, 1625, 1650, 1675, 1700, 1725, 1750, 1775, and 1800, as long as T3(propane)1<T3(propane)2.

The conversion of propane in the process of the present invention can be desirably high, generally higher than 70% (desirably higher than 80%) and lower than 99%. At higher than 96%, the total selectivity toward ethene and propene can be low. Thus, the conversion of propane can be from ConP(1)% to ConP(2)%, where ConP(1) and ConP(2) can be, independently, 70, 72, 74, 76, 78, 80, 82, 84, 85, 86, 88, 90, 92, 94, 96, 98, 99, and 100, as long as Con(1)<Con(2).

Butane Steam Cracking

For butane cracking, preferred fresh feed to the steam cracking reactor comprises from 50-100 mol % (e.g., 50, 55, 60, 65, 70, 75, 80, 85, 90, 95, 96, 97, 98, 99, or 100 mol %) of butane. As a minor component, propane may be present in the total hydrocarbon feed material as well, e.g., at a concentration from 5% to 50% by mole (e.g., 5, 10, 15, 20, 25, 30, 35, 40, 45, 50 mol %) of the total hydrocarbon feed. As another minor component, $C_5H_{10}$ may be present in the total hydrocarbon feed material, e.g., at a concentration from 0% to 10% by mol of the total hydrocarbon feed. Under the cracking conditions, especially in the radiant section where the temperature is high, the cracking of propane, butane, $C_5H_{10}$ and ethane are favored to produce methane, ethene, propene, hydrogen, acetylene, and methylacetylene, which are smaller in molecular weight than propane. Larger molecules, such as C4, C5, and C6 hydrocarbons, may be produced, but typically at low concentrations. Upon separation in down-stream processes, C4, C5, and C6 olefins and aromatics can be obtained as valuable byproducts, and residual butane, ethane and propane can be recycled to the steam cracking furnace as a portion of the overall feed.

T1 can be in the range from T1(butane)1 to T1(butane)2° F., where T1(butane)1 and T1(butane)2 can be, independently, 1150, 1175, 1200, 1225, 1250, 1275, 1300, 1325, 1350, 1375, 1400, as long as T1(butane)1<T1(butane)2;

T2 can be in the range from T2(butane)1 to T2(butane)2° F., where T2(butane)1 and T2(butane)2 can be, independently, about 25 to 150° F. (14 to 83° C.) lower than T1, as long as T2(butane)1<T2(butane)2; and T3 can be in the range from T3(butane)1 to T3(butane)2° F., where T3(butane)1 and T3(butane)2 can be, independently, 1500, 1525, 1550, 1575, 1600, 1625, 1650, 1675, 1700, 1725, 1750, 1775, 1800, as long as T3(butane)1<T3(butane)2.

In the steam cracking process of the present invention for butane, it is highly desirable that the total concentration of C5 and C6 olefins, dienes and benzene in the cracked fluid mixture is in a range from x3 mol % to x4 mol % based on the total moles of different species therein, where x3 and x4 can be, independently, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, as long as x3<x4.

In the steam cracking process of the present invention for butane, it is highly desirable that process has a total severity index (SI) in the cracked fluid mixture in a range from s3 to s4, where s3 and s4 can be, independently, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, as long as s3<s4.

Naphtha Steam Cracking

For naphtha cracking:

T1 can be in the range from T1(naphtha)1 to T1(naphtha)2° F., where T1(naphtha)1 and T1(naphtha)2 can be, independently, 1150, 1175, 1200, 1225, 1250, as long as T1(naphtha)1<T1(naphtha)2;

T2 can be in the range from T2(naphtha)1 to T2(naphtha)2° F., where T2(naphtha)1 and T2(naphtha)2 can be, independently, 1125, 1150, 1175, 1200, 1225, 1245, as long as T2(naphtha)1<T2(naphtha)2; and T3 can be in the range from T3(naphtha)1 to T3(naphtha)2° F., where T3(naphtha)1 and T3(naphtha)2 can be, independently, 1450, 1475, 1500, 1525, 1550, 1575, 1600, as long as T3(naphtha)1<T3(naphtha)2.

In the steam cracking process of the present invention for naphtha, it is highly desirable that the total concentration of C5 and C6 olefins, dienes and benzene in the cracked fluid mixture is in a range from x5 mol % to x6 mol % based on the total moles of different species therein, where x5 and x6 can be, independently, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, as long as x5<x6.

In the steam cracking process of the present invention for naphtha, it is highly desirable that process has a total severity index (SI) in the cracked fluid mixture in a range from s5 to s6, where s5 and s6 can be, independently, 0.50, 0.55, 0.60, 0.65, 0.70, 0.75, 0.80, 0.85, 0.90, 0.95, 1.00, 1.05, 1.10, 1.15, 1.20, 1.25, as long as s5<s6.

Gas Oil Steam Cracking

For gas oil cracking:

T1 can be in the range from T1(GO)1 to T1(GO)2° F., where T1(GO)1 and T1(GO)2 can be, independently, 1060, 1075, 1100, 1125, 1150, 1160, as long as T1(GO)1<T1(GO)2;

T2 can be in the range from T2(GO)1 to T2(GO)2° F., where T2(GO)1 and T2(GO)2 can be, independently, 1035, 1050, 1075, 1100, 1125, 1150, 1155, as long as T2(GO)1<T2(GO)2; and T3 can be in the range from T3(GO)1 to T3(GO)2° F., where T3(GO)1 and T3(GO)2 can be, independently, 1375, 1400, 1425, 1450, 1475, 1500, 1525, as long as T3(GO)1<T3(GO)2.

In the steam cracking process of the present invention for gas oil, it is highly desirable that the total concentration of C5 and C6 olefins, dienes and benzene in the cracked fluid mixture is in a range from x7 mol % to x8 mol % based on the total moles of different species therein, where x7 and x8 can be, independently, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, as long as x7<x8.

In the steam cracking process of the present invention for gas oil, it is highly desirable that process has a total severity index (SI) in the cracked fluid mixture in a range from s7 to s8, where s7 and s8 can be, independently, 0.8, 1.0, 1.1, 1.2, 1.3, 1.4, 1.5, 1.7, 1.8, 1.9, 2.0, 2.1, 2.2, 2.4, as long as s7<s8. Examples include an SI from 1.3 to 1.8.

The following non-limiting examples further illustrate the present invention.

EXAMPLES

The following examples of steam cracking processes were run in industrial reactors.

Example 1

An ethane feed having an average composition (wt %) as follows was used:

| | |
|---|---|
| C5+ and heavier | 0.02 |
| Propane | 0.47 |
| Propene | 0.25 |
| 1-Butene | 0.03 |
| 2-Butene | 0.01 |
| Ethene | 0.78 |
| Ethane | 97.53 |
| Methane | 0.91 |

The ethane feed was fed into a steam cracking furnace in five different runs with the following conditions of temperature at the end of the convection section (T1, which is also the temperature at the beginning of the cross-over section), pressure at the end of the convection section (P1), temperature at the outlet of the radiant section (T3), pressure at the outlet of the radiant section (P3), and firing rate in the furnace identified in TABLE I below. Conversion of ethane was calculated from the measured composition of the cracked fluid mixture and reported in TABLE I as well.

TABLE I

| Run No. | | 1 | 2 | 3 |
|---|---|---|---|---|
| T1 | (° F.) | 1350 | 1356 | 1358 |
| | (° C.) | 732.2 | 735.6 | 736.7 |
| P1 (absolute) | (psi) | 67.7 | 65.9 | 63.7 |
| | (kPa) | 6838 | 6656 | 6434 |
| T3 | (° F.) | 1597 | 1617 | 1631 |
| | (° C.) | 869.4 | 880.6 | 888.3 |
| P3 (absolute) | (psi) | 33.7 | 33.7 | 33.85 |
| | (kPa) | 3404 | 3404 | 3419 |
| Flow Rate | (Pounds/hour/furnace) | 40,920 | 38,990 | 37,750 |
| Ethane Conversion | (%) | 70.5 | 76.1 | 80 |
| Furnace Firing Rate | (MBtu/hour) | 130 | 130 | 130 |

Compositions of the gas mixture sampled at the cross-over section were analyzed for each run described in TABLE I above, and reported in TABLE II below.

TABLE II

| Run No. | | 1 | 2 | 3 |
|---|---|---|---|---|
| C2 Conversion @ Cross-Over Section | | 18 | 20 | 21 |
| Final C2 Conversion (%) | | 70 | 75 | 80 |
| Severity | | 0.353 | 0.205 | 0.247 |
| Ethene Selectivity (%) | | 11.165 | 11.222 | 10.313 |
| T1 (° F.) | | 1350 | 1356 | 1358 |
| Composition (wt %) | Hydrogen | 1.06 | 1.24 | 1.38 |
| | Methane | 1.44 | 1.58 | 1.81 |
| | Acetylene | 0.00 | 0.00 | 0.00 |
| | Ethene | 16.09 | 17.78 | 18.70 |
| | Ethane | 75.89 | 77.88 | 78.70 |
| | Propene | 0.51 | 0.49 | 0.45 |
| | Propane | 0.34 | 0.24 | 0.21 |
| | $C_4H_6$ | 0.09 | 0.11 | 0.12 |
| | 1-Butene | 0.12 | 0.14 | 0.14 |
| | 2-Butene | 0.03 | 0.04 | 0.04 |
| | 1-Butylene | 0.00 | 0.00 | 0.00 |
| | n-Butane | 0.23 | 0.26 | 0.28 |
| | Iso-Butane | 0.00 | 0.00 | 0.00 |
| | Total C4 hydrocarbons | 0.48 | 0.54 | 0.57 |
| | Cyclopentadiene | 0.01 | 0.02 | 0.02 |
| | Methylcyclopentadiene | 0.00 | 0.00 | 0.00 |
| | Isoprene | 0.00 | 0.00 | 0.00 |
| | Total C5 hydrocarbons | 0.05 | 0.06 | 0.08 |
| | Benzene | 0.01 | 0.02 | 0.02 |
| | Toluene | 0.00 | 0.00 | 0.00 |
| | Styrene | 0.00 | 0.00 | 0.00 |
| | Xylene | 0.00 | 0.00 | 0.00 |
| | Total C5+ | 0.13 | 0.16 | 0.16 |
| | Total SCN | 0.12 | 0.16 | 0.15 |
| | SOGO | 0.02 | 0.00 | 0.01 |
| | Tar | 0.00 | 0.00 | 0.00 |

Compositions of two samples of cracked fluid mixture collected at the end of the radiant section for each run of run Nos. 1 and 2 above were analyzed and provided in TABLE IIa below. The end of the radiant section is located out of but in close proximity to the cracking furnace. The samples analyzed are believed to represent the compositions of the cracked fluid mixture at the end of the radiant section because immediately before or after sample collection, the samples were quenched to stop further cracking and other reactions therein.

TABLE IIa

| Case No. of Runs | | | 1A | 1B | 2A | 2B |
|---|---|---|---|---|---|---|
| C2 Conversion | | | 70.4 | 70.5 | 76.5 | 75.7 |
| Severity | | | 0.231 | 0.229 | 0.199 | 0.204 |
| Ethene Selectivity in Radiant Section (%) | | | 8.089 | 8.056 | 6.845 | 6.960 |
| T3 | (° F.) | | 1597 | 1597 | 1617 | 1617 |
| | (° C.) | | 869 | 869 | 880 | 880 |
| Composition (wt %) | Hydrogen | | 4.20 | 4.26 | 4.58 | 4.53 |
| | Methane | | 6.52 | 6.54 | 8.00 | 7.83 |
| | Acetylene | | 0.57 | 0.57 | 0.78 | 0.76 |
| | Ethene | | 52.76 | 52.70 | 54.79 | 54.50 |
| | Ethane | | 28.88 | 28.75 | 22.97 | 23.66 |
| | Methylacetylene and propadiene | | 0.07 | 0.08 | 0.10 | 0.10 |
| | Propene | | 1.51 | 1.50 | 1.59 | 1.59 |
| | Propane | | 0.18 | 0.18 | 0.15 | 0.16 |
| | $C_4H_6$ | | 1.88 | 1.89 | 2.23 | 2.18 |
| | 1-Butene | | 0.14 | 0.14 | 0.15 | 0.15 |
| | 2-Butene | | 0.00 | 0.00 | 0.00 | 0.00 |
| | 1-Butylene | | 0.19 | 0.19 | 0.14 | 0.15 |
| | n-Butane | | 0.00 | 0.00 | 0.00 | 0.00 |
| | Isobutane | | 2.43 | 2.44 | 2.76 | 2.72 |
| | Cyclopentadiene | | 0.52 | 0.50 | 0.68 | 0.65 |
| | Methylcyclopentadiene | | 0.00 | 0.00 | 0.00 | 0.00 |
| | Isoprene | | 0.04 | 0.04 | 0.04 | 0.04 |
| | Total C5's | | 0.83 | 0.76 | 0.97 | 0.94 |
| | Benzene | | 1.21 | 1.19 | 2.04 | 1.88 |
| | Toluene | | 0.15 | 0.14 | 0.26 | 0.23 |
| | Styrene | | 0.09 | 0.09 | 0.17 | 0.16 |
| | Xylene | | 0.01 | 0.03 | 0.03 | 0.03 |
| | Total C5+ | | 2.71 | 2.73 | 4.02 | 3.87 |
| | Total Steam-Cracked Naphtha | | 2.68 | 2.59 | 3.93 | 3.71 |
| | Steam-Cracked Gas Oil | | 0.03 | 0.14 | 0.10 | 0.16 |
| | Tar | | 0.00 | 0.00 | 0.00 | 0.00 |

As can be seen from the data in TABLE II, as T1 increased from about 1350 to 1373° F., the C2 conversion in the cross-over section increased from 18% to 27%, and the selectivity of ethene in the cross-over section only decreased slightly from 11.165% to about 9.582%.

As can be seen from the data in TABLE IIa, as T1 increased from 1350° F. in run No. 1 to 1356° F. in run No. 2, ethane conversion in the cross-over section increased from 18% to 20%, ethane final conversion at the end of the radiant section increased by about 5%, but the final selectivity at the end of the radiant section toward ethene was essentially unchanged: both at about 49%. It is believed that the increase of temperature in the lower portion of the convection section and the cross-over section, therefore a higher conversion in the convection section and the cross-over section, would require a lower temperature in the radiant section in order to achieve the overall same level of selectivity toward ethene at the end of the radiant section. A lower temperature in the radiant section would require less thermal input from the flames inside the furnace. This would result in the less formation of coke on the internal wall of the radiant section, thereby extending the run-length between required adjacent decoking sessions.

Example 2

A butane feed having an average composition (wt %) as follows was used:

| | |
|---|---|
| Hydrogen | 0.02 |
| Propane | 0.11 |
| Propene | 0.01 |
| Isobutane | 1.47 |
| n-Butane | 97.12 |
| Isobutene | 0.29 |
| t2-Butene | 0.04 |
| Ethane | 0.02 |
| Methane | 0.03 |
| C5 & heavier | 0.81 |

The butane feed was fed into a steam cracking furnace in 16 runs (with the following conditions of temperature at the end of the convection section (T1), pressure at the end of the convection section (P1), temperature at the outlet of the radiant section (T3), pressure at the outlet of the radiant section (P3), and firing rate in the furnace identified in TABLE Ma and Mb below. Conversion of butane was calculated from the measured composition of the cracked fluid mixture and reported in TABLE IIIa and IIIb as well. Note for Run Nos. 1A, 1B, 2A, 2B, 3A, 3B, 4A, 4B, 5A, 5B, 6A, 6B, 7A, and 7B, all conversion, severity and selectivity data are for the overall process including the convection section, the cross-over section and the radiant section, and composition data for Run Nos. 7A and 7B are for samples collected at the end of the radiant section. However, for Run Nos. 8A and 8B, the conversion, severity, selectivity and composition data are for samples collected at the end of cross-over section before the radiant section. All these exemplary runs were conducted at cross-over temperatures (T1) where significant butane steam-cracking occurs.

TABLE IIIa

| | | Run No. | | | | | | | |
|---|---|---|---|---|---|---|---|---|---|
| | | 1A | 1B | 2A | 2B | 3A | 3B | 4A | 4B |
| Conversion | (wt %) | 89.63 | 89.79 | 89.94 | 89.34 | 93.98 | 94.48 | 95.68 | 96.29 |
| | Severity | 1.049 | 1.044 | 1.024 | 1.051 | 0.8 | 0.808 | 0.75 | 0.709 |
| | Selectivity | 1.688 | 1.687 | 1.74 | 1.746 | 1.713 | 1.716 | 1.648 | 1.638 |
| T3 | (° F.) | 1536 | 1537 | 1538 | 1536 | 1563 | 1564 | 1570 | 1568 |
| | (° C.) | 835.6 | 836.1 | 836.7 | 835.6 | 850.6 | 851.1 | 854.4 | 853.3 |
| T1 | (° F.) | 1286 | 1287 | 1290 | 1289 | 1291 | 1289 | 1300 | 1300 |
| | (° C.) | 696.7 | 697.2 | 698.9 | 698.3 | 699.4 | 698.3 | 704.4 | 704.4 |
| P3 | (psig) | 12 | 12 | 12 | 12 | 12 | 12 | 12 | 12 |
| | (kPa, Gauge) | 83 | 83 | 83 | 83 | 83 | 83 | 83 | 83 |
| P1 (absolute) | (psi) | | | | | 46 | | 42.1 | |
| | (kPa) | | | | | 317 | | 290 | |
| Steam/Oil Ratio | (wt) | 0.3 | 0.3 | 0.5 | 0.5 | 0.5 | 0.5 | 0.3 | 0.3 |
| Feed Rate | (kilo-pounds per hour, Quad) | 10.6 | 10.2 | 9.7 | 9.8 | 9 | 9.1 | 9.2 | 9.1 |
| Firing Rate | (MBTU/Hour) | 107 | 107 | 107 | 108 | 108 | 108 | 108 | 107 |

TABLE IIIb

| | | Run No. | | | | | | | |
|---|---|---|---|---|---|---|---|---|---|
| | | 5A | 5B | 6A | 6B | 7A | 7B | 8A* | 8B* |
| Conversion | (wt %) | 97.72 | 97.84 | 99.06 | 99.02 | 98.92 | 99.04 | 24.81 | 24.54 |
| | Severity | 0.594 | 0.583 | 0.448 | 0.453 | 0.47 | 0.458 | 2.434* | 2.433* |
| | Selectivity | 1.545 | 1.54 | 1.555 | 1.555 | 1.613 | 1.616 | 1.312* | 1.306* |
| T3 | (° F.) | 1574 | 1574 | 1606 | 1608 | 1615 | 1615 | 1563 | 1563 |
| | (° C.) | 856.7 | 856.7 | 874.4 | 875.6 | 879.4 | 879.4 | 850.6 | 850.6 |
| T1 | (° F.) | 1291 | 1291 | 1294 | 1292 | 1291 | 1289 | 1290 | 1290 |
| | (° C.) | 699.4 | 699.4 | 701.1 | 700 | 699.4 | 698.3 | 698.9 | 698.9 |
| P3 | (psig) | 18 | 18 | 12 | 12 | 12 | 12 | 12 | 12 |
| | (kPa, Gauge) | 124 | 124 | 83 | 83 | 83 | 83 | 83 | 83 |

TABLE IIIb-continued

| | | Run No. | | | | | | | |
|---|---|---|---|---|---|---|---|---|---|
| | | 5A | 5B | 6A | 6B | 7A | 7B | 8A* | 8B* |
| P1 (absolute) | (psi) (kPa) | 45.9 316 | | | | | | | |
| Steam/Oil Ratio | (wt) | 0.3 | 0.3 | 0.3 | 0.3 | 0.5 | 0.5 | 0.5 | 0.5 |
| Feed Rate | (kilo pounds per hour, Quad) | 9.1 | 9 | 8.2 | 8.2 | 7.8 | 7.8 | 7.8 | 7.8 |
| Firing Rate | (MBTU/Hour) | 107 | 107 | 108 | 108 | 108 | 108 | 108 | 108 |

*Data are for samples collected at the end of the cross-over section before the radiant section.

TABLE IV

| | Run No. | | | |
|---|---|---|---|---|
| Component Name | 7A | 7B | 8A* | 8B* |
| Hydrogen | 1.183 | 1.191 | 0.149 | 0.147 |
| Carbon Dioxide | 0.000 | 0.000 | 0.000 | 0.000 |
| Ethene | 38.861 | 38.985 | 5.747 | 5.664 |
| Ethane | 4.113 | 4.067 | 2.174 | 2.149 |
| Acetylene | 0.971 | 1.008 | 0.024 | 0.027 |
| Nitrogen | 1.102 | 1.093 | 0.145 | 0.138 |
| Methane | 24.099 | 24.127 | 4.382 | 4.337 |
| Carbon Monoxide | 0.041 | 0.074 | 0.000 | 0.013 |
| Propane | 0.278 | 0.273 | 0.266 | 0.270 |
| Propene | 11.338 | 11.046 | 10.667 | 10.550 |
| Isobutane | 0.014 | 0.011 | 1.145 | 1.158 |
| Cyclopropane | 0.000 | 0.000 | 0.000 | 0.000 |
| Propadiene | 0.284 | 0.286 | 0.000 | 0.000 |
| n-Butane | 1.048 | 0.934 | 73.025 | 73.289 |
| 1-Butene | 0.398 | 0.374 | 0.533 | 0.530 |
| Isobutene | 0.259 | 0.249 | 0.514 | 0.515 |
| Methylacetylene | 0.510 | 0.519 | 0.022 | 0.023 |
| t-2-Butene | 0.152 | 0.148 | 0.299 | 0.298 |
| c-2-Butene | 0.148 | 0.139 | 0.205 | 0.206 |
| 1,3-Butadiene | 3.643 | 3.648 | 0.136 | 0.133 |
| Ethylacetylene | 0.000 | 0.000 | 0.000 | 0.000 |
| Vinylacetylene | 0.123 | 0.134 | 0.161 | 0.176 |
| 1,2-Butadiene | 0.020 | 0.052 | 0.000 | 0.000 |
| 1-Butene | 0.000 | 0.000 | 0.004 | 0.016 |
| Pentane | 0.000 | 0.000 | 0.143 | 0.154 |
| 1,4-pentadienes | 0.039 | 0.040 | 0.000 | 0.000 |
| Dimethylacetylene | 0.024 | 0.040 | 0.000 | 0.000 |
| 1-Pentene | 0.050 | 0.039 | 0.087 | 0.093 |
| 2-Methyl-1-Butene | 0.000 | 0.000 | 0.012 | 0.012 |
| n-Pentane | 0.000 | 0.000 | 0.010 | 0.012 |
| Isoprene | 0.194 | 0.205 | 0.011 | 0.010 |
| t2-Pentane | 0.000 | 0.000 | 0.010 | 0.010 |
| 3-methyl-1,2-butadiene | 0.000 | 0.000 | 0.000 | 0.000 |
| c2-Pentene | 0.000 | 0.000 | 0.010 | 0.013 |
| 2-Methyl-2-Butene | 0.000 | 0.000 | 0.000 | 0.000 |
| 1-t3-Pentadiene | 0.142 | 0.145 | 0.009 | 0.005 |
| Cyclopentadiene | 1.620 | 1.697 | 0.011 | 0.014 |
| 2,2-Dimethylbutane | 0.000 | 0.000 | 0.000 | 0.000 |
| 1,c3-pentadienes | 0.112 | 0.108 | 0.000 | 0.000 |
| Cyclopentene | 0.077 | 0.077 | 0.019 | 0.008 |
| 3T,4-methyl-1-pentene | 0.000 | 0.000 | 0.008 | 0.013 |
| Cyclopentane | 0.000 | 0.000 | 0.000 | 0.000 |
| 2,3-Dimthylbutane | 0.000 | 0.000 | 0.000 | 0.000 |
| 2,3-Dimethyl-1-butene | 0.000 | 0.000 | 0.000 | 0.000 |
| 2-Methylpentane | 0.000 | 0.000 | 0.000 | 0.000 |
| 4-Methyl-t2-pentadiene | 0.000 | 0.000 | 0.000 | 0.000 |
| 3-Methyl-1,4-pentadiene | 0.000 | 0.000 | 0.008 | 0.008 |
| 3-Methylpentane | 0.000 | 0.000 | 0.000 | 0.000 |
| 2-Methyl-1-pentene | 0.000 | 0.000 | 0.016 | 0.000 |
| T3-Hexene | 0.000 | 0.000 | 0.005 | 0.000 |

*Data are for samples collected at the end of the cross-over section before the radiant section.

Data of Run Nos. 8A and 8B clearly show that at a cross-over temperature (T1) of 1290° F. (698.9° C.), conversion of butane in the cross-over section reached at a level of close to 25%. Run Nos. 3A, 3B, 5A, 5B, 7A, 7B, 8A, and 8B have very similar conditions before the fluid stream enters the radiant section. The temperatures at the end of the radiant section (T3) increases from Run Nos. 3A/3B and 8A/8B (about 1563° F.) to Run Nos. 5A/5B (1574° F.) to Run Nos. 7A/7B (1615° F.). The conditions in Run Nos. 3A/3B/8A/8B are almost identical in terms of T1, P1, T3, and P3. Thus, it can be expected that in all Run Nos. in TABLEs IIIa and IIIb, significant cracking occurs in the cross-over section and part of the convection section. Data in TABLES Ma and IIIb clearly show that the overall conversion in Run Nos. 3A/3B (which presumably corresponds to those in Run Nos. 8A/8B) is only slightly smaller than in Run Nos. 7A/7B, and the selectivity in Run Nos. 3A/3B is slightly higher than in Run Nos. 7A/7B, and the severity in Run Nos. 3A/3B is significantly lower than in Run Nos. 7A/7B, even though the radiant section temperature T3 in Run Nos. 7A/7B (1615° F.) is much higher than in Run Nos. 3A/3B/8A/8B (1563° F.). These data show that where the cross-over section temperature (T1) is sufficiently high to allow for significant cracking in the cross-over sections before the fluid stream is fed into the radiant section, one can use a substantially lower radiant section temperature (T3) to achieve an overall high conversion, selectivity, and more favorable severity.

Example 3

A gas oil feed having an average composition (wt %) and properties in TABLE Va as follows was used:

TABLE Va

| Hydrocarbon Components (wt %) | n-Paraffins | 15.70 |
|---|---|---|
| | Isoparaffins | 14.15 |
| | Naphthenes | 38.09 |
| | Aromatics | 32.06 |
| | Total | 100.00 |
| Elemental Analysis (wt %) | Hydrogen | 13.25 |
| | Carbon | 86.75 |
| | Sulfur | 0.14 |
| Naphthenes Ring Breakdown | One Ring | 12.32 |
| | Two Rings | 12.59 |
| | Three Rings | 8.42 |
| | Four Rings | 4.76 |
| | Total | 38.09 |
| Asphaltenes | | 0.0 |
| Properties | Mean Average Boiling Point (° F.) | 551 |
| | Molecular Weight | 225 |
| | Bureau of Mines Combustion Index | 33.46 |
| | Color | 22 |
| | API Gravity | 34.5 |
| | Specific Gravity | 0.8524 |

The gas oil feed was fed into a steam cracking furnace (with the following conditions of temperature at the end of the convection section (T1), pressure at the end of the convection section (P1), temperature at the outlet of the radiant section (T3), pressure at the outlet of the radiant section (P3), and firing rate in the furnace identified in TABLE V below. Conditions at the end of the radiant section and at the end of the cross-over section, as well compositions of the cracked fluid mixtures at the end of the radiant section and the cross-over fluid stream were analyzed and provided in TABLE VI below.

TABLE V

| Conditions | | Radiant Section | Cross-Over Section |
|---|---|---|---|
| Severity | Measurement No. 1 | 1.541 | 2.059 |
| | Measurement No. 2 | 1.503 | 1.5 |
| Selectivity | Measurement No. 1 | 1.957 | 1.903 |
| | Measurement No. 2 | 1.98 | 1.984 |
| T3 | (° F.) | 1487 | 1486 |
| | (° C.) | 808.3 | 807.8 |
| T1 | (° F.) | 1162 | 1161 |
| | (° C.) | 627.8 | 627.2 |
| P3 | (psi, gauge) | 22.5 | 22.5 |
| | (kPa, Gauge) | 155 | 155 |
| P1 | (psi, gauge) | 34 | 34 |
| | (kPa, Gauge) | 234 | 234 |
| Feed Rate | (kilo pounds per hour) | 14.64 | 14.29 |
| Firing Rate | (MBTU per hour) | 265 | 264.9 |
| Steam/Oil Ratio | (wt) | 0.45 | 0.45 |

TABLE VI

| Component Name | Radiant Cracked Fluid Stream Composition (wt %) | Cross-Over Stream Composition (wt %) |
|---|---|---|
| Hydrogen | 0.403 | 0.053 |
| Carbon dioxide | 0.000 | 0.000 |
| Ethene | 16.473 | 3.225 |
| Ethane | 4.146 | 1.669 |
| Acetylene | 0.122 | 0.004 |
| Nitrogen | 0.166 | 0.015 |
| Methane | 8.412 | 1.695 |
| Carbon monoxide | 0.000 | 0.000 |
| Propane | 0.735 | 0.469 |
| Propene | 12.959 | 3.489 |
| Isobutane | 0.043 | 0.020 |
| Cyclopropane | 0.001 | 0.000 |
| Propadiene | 0.122 | 0.000 |
| n-Butene | 0.112 | 0.067 |
| 1-Butene | 2.686 | 1.181 |
| Isobutene | 2.233 | 0.753 |
| Methylacetylene | 0.126 | 0.007 |
| t2-Butene | 0.718 | 0.260 |
| c2-Butene | 0.450 | 0.138 |
| 1,3-Butadiene | 4.077 | 0.487 |
| Ethylacetylene | 0.002 | 0.000 |
| Vinylacetylene | 0.004 | 0.000 |
| 1,2-Butadiene | 0.036 | 0.003 |
| 3-Methyl-1-Butene | 0.154 | 0.147 |
| Isopentane | 0.023 | 0.009 |
| 1,4-pentadiene | 0.118 | 0.042 |
| Dimethylacetylene | 0.000 | 0.000 |
| 1-Pentene | 0.481 | 0.948 |
| 2-Methyl-1-butene | 0.442 | 0.309 |
| n-Pentane | 0.26 | 0.029 |
| Isoprene | 1.114 | 0.218 |
| T2-Pentene | 0.287 | 0.128 |
| 3-Methyl-1,2-butadiene | 0.000 | 0.000 |
| c2-Pentane | 0.185 | 0.074 |
| 2-Methyl-2-butene | 0.208 | 0.139 |
| 1-t3-pentadiene | 0.541 | 0.192 |
| Cyclopentadiene | 1.525 | 0.173 |
| 2,2-Dimethylbutane | 0.009 | 0.034 |
| 1,c3-Pentadiene | 0.335 | 0.094 |
| Cyclopentene | 0.219 | 0.205 |
| 3&4-Methyl-1-pentene | 0.033 | 0.277 |
| Cyclopentane | 0.021 | 0.008 |
| 2,3-Dimethyl-butane | 0.000 | 0.001 |
| 2,3-Dimethyl-1-butene | 0.016 | 0.024 |
| 2-Methyl-pentane | 0.010 | 0.009 |
| 4-Methyl-t2-pentene | 0.053 | 0.030 |

As can be seen from the above TABLEs V and VI, significant cracking reactions occurred in the convention section and the cross-over section, leading to the presence of substantial amounts of cracked products (ethene, propene, and the like) in the composition of the cross-over fluid stream. This allowed for running the cracking reactions in the radiant section at a reduced temperature of 1486° F. and a reduce severity of the conditions. In general, such milder cracking conditions in the radiant section lead to lower propensity of coke deposition on the inner walls of the radiant section, and hence a longer run-length between required de-coking sessions. In addition, the cracking conditions resulted in the production of ethene, propene, butene, butadiene, and cyclopentadiene at high concentrations, all of which can be valuable products upon separation from the cracked fluid mixture.

What is claimed is:

1. A process for steam cracking a hydrocarbon material in a steam cracking furnace including a tube comprising a convection section, a cross-over section downstream of the convection section, and a heated radiant section downstream of the cross-over section, comprising:
   feeding the hydrocarbon material and steam into the convection section to obtain a mixture comprising the hydrocarbon material and the steam;
   heating the mixture comprising the hydrocarbon material and the steam in the convection section to obtain a first fluid stream at a temperature T1 at the end of the convection section;
   passing the first fluid stream through the cross-over section to obtain a second fluid stream at the end of the cross-over section at a temperature T2;
   passing the second fluid stream through the radiant section to obtain a cracked fluid mixture at the end of the radiant section at a temperature T3, wherein:
   T3 is higher than T2 and T1; and
   T1 and T2 are selected such that significant cracking reaction occurs at least in a portion of the convection section and at least in a portion of the cross-over section;
   the hydrocarbon material comprises one or more olefins at a total concentration of C0 mol % based on the total moles of the fluid species in the hydrocarbon material;
   the second fluid stream comprises one or more olefins at a total concentration of C2 mol % based on the total moles of the fluid species therein; and
   C2−C0 is ≥5.

2. The process of claim 1, wherein:
   the first fluid stream comprises one or more olefins at a total concentration of C1 mol % based on the total moles of the fluid species therein, and
   C1−C0 is ≥1.

3. The process of claim 2, wherein:
   C2−C1 is ≥1.

4. The process of claim 1, wherein the hydrocarbon material comprises ethane at a concentration of at least 50 mol % based on the total moles of hydrocarbons in the hydrocarbon material, and T1 is in a range from 1300° F. to 1435° F.

5. The process of claim 4, wherein T2 is in a range from 1275° F. to 1430° F.

6. The process of claim 4, wherein T3 is in a range from 1500° F. to 1800° F.

7. The process of claim 4, wherein a total concentration of C5 and C6 olefins and benzene in the cracked fluid mixture is in a range from 1 mol % to 8 mol %, based on a total moles of species therein.

8. The process of claim 4, wherein an overall conversion of ethane in the steam cracking furnace is in a range from 60% to 75%.

9. The process of claim 1, wherein the hydrocarbon material comprises propane at a concentration of at least 50 mol % based on the total moles of hydrocarbons in the hydrocarbon material, and T1 is in a range from 1200° F. to 1415° F.

10. The process of claim 9, wherein T2 is in a range from 1175° F. to 1410° F.

11. The process of claim 9, wherein T3 is in a range from 1525° F. to 1800° F.

12. The process of claim 9, wherein an overall conversion of propane in the steam cracking furnace is in a range from 80% to 96%.

13. The process of claim 1, wherein the hydrocarbon material comprises butane at a concentration of at least 50 mol % based on the total moles of hydrocarbons in the hydrocarbon material, and T1 is in a range from 1150° F. to 1400° F.

14. The process of claim 13, wherein T2 is from 25° F. to 150° F. lower than T1.

15. The process of claim 13, wherein T3 is in a range from 1475° F. to 1700° F.

16. The process of claim 13, having a severity index in the cracked fluid mixture in a range from 0.50 to 1.65.

17. The process of claim 1, wherein the hydrocarbon material comprises naphtha at a concentration of at least 50 mol % based on the total moles of the hydrocarbon material, and T1 is in a range from 1150° F. to 1250° F.

18. The process of claim 17, wherein T2 is in a range from 1125° F. to 1245° F.

19. The process of claim 17, wherein T3 is in a range from 1450° F. to 1600° F.

20. The process of claim 17, having a severity index in the cracked fluid mixture in a range from 0.50 to 1.25.

21. The process of claim 1, wherein the hydrocarbon material comprises a gas oil at a concentration of at least 50 mol % based on the total moles of hydrocarbons in the hydrocarbon material, and T1 is in a range from 1060° F. to 1160° F.

22. The process of claim 21, wherein T2 is in a range from 1035° F. to 1155° F.

23. The process of claim 21, wherein T3 is in a range from 1375° F. to 1525° F.

24. The process of claim 21, having a severity index in the cracked fluid mixture in a range from 0.8 to 2.4.

25. A process for steam cracking a hydrocarbon, comprising:
   introducing a hydrocarbon and steam into a convection section of a steam cracking furnace to produce a mixture comprising the hydrocarbon and the steam, wherein the mixture comprising the hydrocarbon and the steam has a first concentration of olefins;
   heating the mixture comprising the hydrocarbon and the steam in the convection section to produce a first cracked mixture having a second concentration of olefins;
   heating the first cracked mixture in a cross-over section of the steam cracking furnace to produce a second cracked mixture having a third concentration of olefins; and
   heating the second cracked mixture in a radiant section of the steam cracking furnace to produce a third cracked mixture having a fourth concentration of olefins, wherein:
   the second concentration of olefins is greater than the first concentration of olefins,
   the third concentration of olefins is greater than the second concentration of olefins,
   the fourth concentration of olefins is greater than the third concentration of olefins, and
   the third concentration of olefins is at least 5 mol % greater than the first concentration of olefins.

* * * * *